United States Patent [19]

Lawless, Jr. et al.

[11] Patent Number: 5,153,134
[45] Date of Patent: Oct. 6, 1992

[54] FERMENTATION OF MICROORGANISMS HAVING ICE NUCLEATION ACTIVITY USING A TEMPERATURE CHANGE

[75] Inventors: Richard J. Lawless, Jr., Rochester; Richard J. LaDuca, Pittsford, both of N.Y.

[73] Assignee: Genencor International, Inc., S. San Francisco, Calif.

[21] Appl. No.: 21,949

[22] Filed: Mar. 5, 1987

[51] Int. Cl.$^5$ .......................... C12N 1/20; C12N 1/38; C12P 1/04

[52] U.S. Cl. .............................. 435/252.1; 435/253.3; 435/244; 435/874; 435/872; 435/170

[58] Field of Search ............... 435/170, 244, 822, 874, 435/252.1, 253.3

[56] References Cited

U.S. PATENT DOCUMENTS

| | | | |
|---|---|---|---|
| 4,021,304 | 5/1977 | Shimamatsu | 435/804 |
| 4,062,727 | 12/1977 | Srinivasan | 435/804 |
| 4,200,228 | 4/1980 | Woerpel | 239/25 |

OTHER PUBLICATIONS

Vining, L. C., *Biochemistry and Genetic Regulation of Commercially Important Antibiotics*, Addison-Wesley 1983, pp. 196-197.

*Difo Manual*, 9th Ed. p. 127.

Stanbury et al., *Principles of Fermentation Technology*, 1984, Pergamon Press pp. 22-24.

Lindow et al, *Phytopathology* 68 (3) 1978, 523-528.

Ice Nucleating Activity of Pseudomonas Syringae and Erwinia Herbicola, vol. 153, No. 1 Journal of Bacteriology, Jan. 1983 pp. 222-231 (Kozloff, Scholfield and Lute).

Bacteria as Biogenic Sources of Freezing Nuclei, L. R. Maki and K. J. Willoughby, Journal of Applied Meterology, 17, pp. 1049-1053.

*Primary Examiner*—Irene Marx

[57] ABSTRACT

A method for the fermentation of microorganisms having a high level of ice nucleating activity is disclosed. A high productivity in the fermentation is achieved by using a certain amount of nitrogen source during the growth phase and low temperature during the stationary phase of the fermentation.

8 Claims, No Drawings

FERMENTATION OF MICROORGANISMS HAVING ICE NUCLEATION ACTIVITY USING A TEMPERATURE CHANGE

FIELD OF THE INVENTION

The present invention relates to a method for the fermentation of microorganisms that have ice nucleating activity.

DESCRIPTION RELATIVE TO THE PRIOR ART

In U.S. Pat. No. 4,200,228 there is disclosed a method for the making of snow whereby microorganisms are included in droplets that are sprayed into the air. The microorganisms that are used are of the type which are known to promote ice nucleation. As a result, snow can be made at temperatures that are much higher than are ordinarily possible. A typical microorganism that is useful in this process is a Pseudomonad and particularly *Pseudomonas syringae*.

It is apparent that if this process is to be used on any scale, large amounts of microorganisms are needed. Further, it is desirable that the microorganism be obtained in a dry form so as to facilitate the storage, handling and transport of the material.

The growth conditions for microorganisms that have ice nucleating activity are known in the art. For example, in Maki and Willoughby, Bacteria as Biogenic Sources of Freezing Nuclei, J. Applied Meteorology 17 1049–1053 it is disclosed that the microorganisms such as *Pseudomonas syringae* are grown in Koser citrate broth at a temperature below 20° C., i.e. 5° C.

In another reference, the microorganisms are grown on a tryptone-yeast extract-glycerol medium which would have a pH of about 7.0. (kozloff, Schofield and Lute, Ice Nucleating Activity of *Pseudomonas syringae* and *Erwinia herbicola*, J. Bacter. 153 pages 222–231 (1983)) In this reference, the microorganisms are not recovered in dry form and the suspensions are tested directly for activity. It is noted that the ice nucleating activity is not stable in the suspension and decreases overnight.

If the known procedures are used for the production of large volumes of the microorganisms, less than the desired ice nucleating activity (INA) is obtained. Not only is the ice nucleating activity of the initial suspension less than desired, but much of the activity is lost during the freeze drying of large volumes of the material. The end result is a process that is not capable of producing commercial quantities of microorganism at reasonable cost.

In U.S. Patent Application Ser. No. 910,600 filed Sep. 23, 1986, there is disclosed an improvement in the processes that were known in the art for the production of ice nucleating microorganisms. In this process, the pH is controlled so as to be between 6.7 and 5.5. As the pH approaches about 6.7, acid is added and as the pH approaches 5.5, base is added. Other improvements to the process for fermenting ice nucleating microorganisms are also disclosed in this application. For example, a preferred medium is disclosed which comprises mannitol as the carbon source and a yeast extract as the nitrogen source.

The method of this reference produces an acceptable INA. For example, the Fermentor INA that is produced according to example 1 of this reference is $5.0 \times 10^{11}$. ("Fermentor INA" as herein defined has the units nuclei per gram of dry cells.) However, the productivity was less than desired. While the fermentation reached a respectable cell density, 18 grams per liter, 36 hours were necessary for completion. As a result, the "Fermentor Productivity", also as herein defined, was only $2.5 \times 10^{11}$ nuclei per L-hour.

In U.S. Patent Application Ser. No. 944,120, filed Dec. 22, 1986, there is disclosed a method that produces better results than those disclosed in the '600 application just mentioned. In example 1, the Fermentor INA was increased to $10 \times 10^{11}$ while the Fermentor Productivity was $6.59 \times 10^{11}$. These results were achieved with a medium which contained a sugar as the carbon source and α-ketoglutarate or an α-ketoglutarate yielding amino acid.

While both of the described applications provide fermentation methods which are greatly improved over those known in the prior art, still further improvements were sought. More particularly, improvements in the Fermentor Productivity were needed to improve the economics of the method.

SUMMARY OF THE INVENTION

The present invention is an improved method for the fermentation of a microorganism having ice nucleating activity comprising the steps of fermenting the microorganism in a medium and recovering the microorganism. The improvement comprises the steps of:

1) growing said microorganism at a temperature of at least about 29° C. in a medium containing a nitrogen source the concentration of which is:
   a) sufficient to provide a cell mass of at least 20 g/L and which
   b) is low enough so that, at the conclusion of the growth phase, there is insufficient nitrogen source remaining to inhibit the formation of ice nucleating activity during the subsequent stationary phase and
2) continuing said fermentation during the stationary phase at a temperature below about 24° C.

DETAILED DESCRIPTION OF THE INVENTION

It will be noted from the above discussion that there are two essential features of the present invention. First, the concentration of the nitrogen source in the growth phase and second, the temperatures during the growth and stationary phases. These features are necessary in order to attain high INA at the same time as providing a high Fermentor Productivity. For example, the cell density in Example 1 of the '120 application mentioned above reached only 14.5 g/L. If the nutrient concentration were increased and the temperature increased and maintained in order to improve cell growth, INA was severely reduced. Similarly, if the temperature were adjusted (even though there is no suggestion to do so), without appropriate adjustments to the nutrient concentration, poor Productivity resulted.

The initial concentration of the nitrogen source is related to the temperature of the fermentation during the growth phase. There should be enough nitrogen source present to provide a final cell mass of at least about 20 g/L. However, there should not be so much that there is inhibitory amounts of nitrogen source left over after the growth phase is completed. The amount is related to temperature since as the temperature is increased, the potential for cell mass is also increased (up to a point) and the nitrogen source must be increased correspondingly. As the optimum growth temperature for the microorganism is exceeded, the potential for growth decreases and the nitrogen source must be decreased accordingly.

In a typical growth phase with *P. syringae* at 30° C. the initial concentration of the nitrogen source will be about 45 g/L (based on monosodium glutamate (MSG)) which will produce a cell mass of about 24 g/L at the end of the growth phase. Little MSG will remain. At 33° C., the optimum growth temperature for this microorganism is exceeded and the concentration should be slightly lower such as about 40 g/L.

The amount of nitrogen source remaining at the conclusion of the growth phase can be measured using conventional methods. The exact method used will depend on the nature of the nitrogen source. Where MSG is the source, it can be measured in the medium by an HPLC method using an OPA-mercaptoethanol fluorescent derivative as is known in the art.

It should be noted that the criteria mentioned usually results in an initial concentration that is somewhat higher than that previously used. At 30° C. for example, the MSG concentration is 45 g/L which will produce a cell density of 24 g/L. In comparison, the initial concentration of the L-glutamic acid in the example in the '120 was 20 g/L at a growth temperature of 24° C.

According to the invention, the nitrogen source should be low enough so that, at the conclusion of the growth phase, there is insufficient nitrogen source remaining to inhibit the formation of ice nucleating activity during the subsequent stationary phase. That is, if more than this amount is used, the INA will decrease by more than about 60%. With several experiments, the exact amount can be determined. Preferably, this means that less than 20 g/L remains at this time in the fermentation medium and still more preferably, less than 5 g/L.

In the fermentation of the present microorganism as well as other microorganisms, there is what is called the growth phase where the microorganism is multiplying rapidly. This phase is also known in the art as the "log phase" or logarithemic growth phase. During this period, if the logarithm of the optical density of the growth medium is plotted versus time, a straight line will result. At the end of this period, the slope of this line will decrease dramatically indicating that the microorganism is no longer proliferating, i.e. the stationary phase is reached. There is a brief transition between these two phases. In a typical fermentation lasting for 22 hours, for example, the transition may last only one hour. When we refer to the "conclusion of the growth phase" we intend to include any time from about the end of the straight line portion through the brief transition period.

The temperature during the growth phase should be above about 29° C. in order to promote good growth. While higher temperatures can be used in the method of the invention, temperatures above about 35° C. are not necessary. For the preferred microorganism used in the present invention, *P. syringae*, growth is reduced at temperatures above 33° C. Very high cell densities can be attained at lower temperatures. The currently preferred temperature during the growth phase is about 30° C.

We have found that the INA is produced predominantly during the stationary phase of the fermentation. Further, during this phase, the temperature must be reduced to below 24° C. for there to be a significant amount of INA produced. While the temperature can be lower than 24° C., little further improvement in INA is observed at temperatures below about 21° C. Therefore, the presently preferred temperature for the stationary phase is 21° C.

While any conventional medium can be used in the practice of the present invention, the medium that is described in U.S. Ser. No. 944,120 cited above is the currently preferred medium. That medium comprises two essential components, a sugar and α-ketoglutarate or an α-ketoglutarate yielding amino acid.

Sugars that are useful include glucose (or crude glucose such as dextrose), sucrose, fructose, erythrose, mannose, xylose and ribose. Commercial sources of these sugars can conveniently be used. Such sources include liquid sucrose, high fructose corn syrup and dextrose corn syrup. Mixtures of these sugars can also be used. Other carbon sources can be used in combination with these sugars such as mannitol and other sugar derivatives.

The other essential component is α-ketoglutarate or an α-ketoglutarate yielding amino acid. Amino acids which yield α-ketoglutarate in biological processes are arginine, histidine, glutamine, glutamic acid and proline. Salts of these acids are also useful, for example, monosodium glutamate (MSG). A discussion of the production of α-ketoglutarate from these amino acids is found in Biochemistry 2nd ed., Lehninger, Worth (1975) page 574 et seq. Mixtures of these compounds can also be used.

The medium also preferably contains phosphates such as potassium phosphates. A useful range of initial phosphate concentration is between about 0.2 to 6 g/L preferably 0.6 to 3 g/L. In preferred embodiments, the initial phosphate concentration is selected so that little, e.g. less than 1 g/L, remains at the conclusion of the growth phase.

The medium preferably contains other components. As is known in the art for the fermentation of these microorganisms, magnesium sulfate is preferred. Also, it is desirable for the medium to contain trace amounts of metals. Trace amounts of iron and zinc are particularly useful.

For use in a fermentation where the growth phase temperature is 30° C., the following medium is preferred:

| | |
|---|---|
| sucrose | 90 g/L |
| MSG | 45 g/L |
| magnesium sulfate | 4 g/L |
| potassium phosphate | 2.75 g/L |
| iron sulfate | .112 g/L |
| zinc sulfate | .0024 g/L |

During the fermentation, it is desirable to control the pH as disclosed in the above mentioned U.S. application Ser. No. 910,600.

Any microorganism that has ice nucleation activity can be produced by the present invention. Suitable microorganisms include Pseudomonads such as *P. syringae* and *P. fluorscens, P. coronafaciens* and *P. pisi*. Other microorganisms that are useful in the present invention include *Erwina herbicola*. The presently preferred microorganism is *P. syringae* ATCC No. 53543 deposited on Sep. 23, 1986 in accordance with the Budapest Treaty with the American Type Culture Collection in Rockville Md., U.S.A.

The microorganism that is produced in the described fermentation can be dried in a number of ways. Spray drying and freeze drying are typical examples. Any drying process will reduce the INA to a certain extent. One preferred method that preserves a large amount of the INA that is produced in the fermentor is the process that is described in commonly assigned U.S. Pat. No. 4,706,463, issued Nov. 7, 1987 entitled "Recovery of Microorganisms Having Ice Nucleating Activity" of Lindsey. In this process, the medium is cooled, concentrated, run into a cryogenic liquid to form pellets and then the pellets are freeze dried at relatively low temperature.

In the examples presented below, the INA is calculated using conventional techniques. The INA is determined by placing a plurality of microorganism containing water droplets (10 μl) on paraffin coated aluminum foil. The foil is maintained at −5° C. by placing it on a constant temperature bath. Details regarding this procedure are found in the literature, for example, Vali, Quantitative Evaluation of Experimental Results on the Heterogenous Freezing of Supercooled Liquids, J. Atoms Sci., 28, 402–409 (1971). The INA reported in the examples is the number of ice nucleating sites per dry gram of microorganism. For the present purposes, the INA is measured using a sample directly from the fermentor without drying. It will therefore be referred to as "Fermentor INA". The units are nuclei per dry gram of microorganism. INA can be measured at frequent intervals to determine the optimum INA production.

Fermentor Productivity in the Table below is defined as the Fermentor INA times the cell mass divided by the time of the fermentation starting with a 10% seed inoculum. The units are nuclei per L-hr.

The following examples are submitted for a further understanding of the invention.

SEED CULTURE

A 4.5 mL sample of *Pseudomonas syringae* ATCC No. 53543 was placed in a 14 L fermentor which contained 5 L of the fermentation medium described above. The temperature was maintained at 30° C. Sulfuric acid was added when the pH approached 6.6. Fermentation in this seed fermentor continued for 21 hours.

EXAMPLES 1-3

A series of fermentations were run to illustrate the invention.

For each fermentation, a 0.5 L sample of the seed culture was transferred to another 14 L fermentor which contained 4.5 L of a medium having the same components. Unless otherwise stated, the concentration of the components was also the same. The temperature was controlled during the fermentation as indicated in the Table. In the table, the first temperature is the temperature during the growth phase and the second temperature is that during the stationary phase. If only one temperature is given, there was no change in the temperature during the fermentation. A sample of the medium was taken at the end of the growth phase and analysed for MSG content. The result is reported in the Table as the "Nit. Conc.". Sulfuric acid was added when the pH reached 6.6 and sodium hydroxide was added when the pH reached 5.6. The dissolved oxygen was maintained at greater than 10% saturation. All fermentations were carried out for 22 hours. Antifoaming agent was added as needed to control foaming. The results are given in the table below.

TABLE

| | Nit. Conc. g/L | Ferm. INA × $10^{11}$ | Cell Mass g/L | Temp °C. | Ferm. Prod. × $10^{11}$ |
|---|---|---|---|---|---|
| Examples of the Invention | | | | | |
| Ex. 1 | 0.0 | 20 | 24 | 30–21 | 21.8 |
| Ex. 2 | 18[1] | 7.26 | 22 | 33–21 | 8.00 |
| Ex. 3 | 7.3 | 7.96 | 25 | 30–24 | 11.6 |
| Comparative Examples | | | | | |
| C1 | 11 | 4.58 | 19 | 27–21 | 3.96 |
| C2 | 14 | 2.19 | 15 | 24–21 | 1.49 |
| C3[2] | NA | 3.17 | 12 | 30–21 | 1.9 |
| C4[3] | NA | 5 | 18 | 21 | 2.5 |
| C5[4] | NA | 10 | 14.5 | 24 | 6.59 |
| C6 | NA | .54 | 24 | 30 | .65 |

NA = not available
[1]Phosphate was the limiting nutrient in this run
[2]Initial MSG concentration 25 g/L
[3]Example 1 of USSN 910,600 (36 hours) complex nitrogen source
[4]Example 1 of USSN 94,120 L-glutamic acid The invention has been described in detail with particular reference to preferred embodiments thereof, but it will be understood that variations and modifications can be effected within the spirit and scope of the invention.

We claim:

1. In a method for the culture of a microorganism having ice nucleating activity comprising the steps of culturing the microorganism in a medium and recovering the microorganism the improvement comprising the steps of:
   1) growing said microorganism at a temperature of at least 29° C. in a medium containing a nitrogen source the concentration of which is:
      a) sufficient to provide a cell mass of at least 20 g/L and which
      b) is low enough so that, at the conclusion of the growth phase, there is insufficient nitrogen source remaining to inhibit the formation of ice nucleating activity during the subsequent stationary phase and
   2) continuing said fermentation during the stationary phase at a temperature below about 24° C.

2. The method according to claim 1 wherein said temperature during step 2) is less than 21° C.

3. The method according to claim 1 wherein the concentration of said nitrogen source at the conclusion of the growth phase is less than 20 g/L.

4. The method according to claim 1 wherein the concentration of said nitrogen source at the conclusion of the growth phase is less than 5 g/L.

5. The method according to claim 1 wherein said medium contains a sugar and α-ketoglutarate or an α-ketoglutarate yielding amino acid.

6. The method according to claim 5 wherein said medium contains sucrose and monosodium glutamate.

7. The method according to claim 1 wherein said microorganism is a *Pseudomonad*.

8. The method according to claim 7 wherein said microorganism is *P. syringae*.

* * * * *